US008846093B2

(12) United States Patent
Govil et al.

(10) Patent No.: US 8,846,093 B2
(45) Date of Patent: Sep. 30, 2014

(54) ADHESIVE MIXTURE FOR TRANSDERMAL DELIVERY OF HIGHLY PLASTICIZING DRUGS

(75) Inventors: Sharad K. Govil, Essex, VT (US); Ludwig J. Weimann, Burlington, VT (US)

(73) Assignee: Mylan Technologies, Inc., Morgantown, WV (US)

( * ) Notice: Subject to any disclaimer, the term of this patent is extended or adjusted under 35 U.S.C. 154(b) by 0 days.

(21) Appl. No.: 13/100,581

(22) Filed: May 4, 2011

(65) Prior Publication Data

US 2012/0083535 A1 Apr. 5, 2012

Related U.S. Application Data

(60) Continuation of application No. 12/286,236, filed on Sep. 29, 2008, now abandoned, which is a continuation of application No. 10/730,561, filed on Dec. 8, 2003, now Pat. No. 7,638,140, which is a division of application No. 09/754,909, filed on Jan. 5, 2001, now Pat. No. 7,070,808, which is a division of application No. 08/883,075, filed on Jun. 26, 1997, now Pat. No. 7,150,881.

(51) Int. Cl.
*A61K 9/14* (2006.01)
*A61K 9/70* (2006.01)
*A61K 31/137* (2006.01)
*A61K 31/138* (2006.01)
*A61K 31/4402* (2006.01)

(52) U.S. Cl.
CPC ............ *A61K 9/7061* (2013.01); *A61K 31/137* (2013.01); *A61K 31/138* (2013.01); *A61K 31/4402* (2013.01)
USPC ............................ 424/487; 424/448; 424/449

(58) Field of Classification Search
USPC .......................................... 424/448, 449, 487
See application file for complete search history.

(56) References Cited

U.S. PATENT DOCUMENTS

| | | | |
|---|---|---|---|
| 4,289,749 A | 9/1981 | Keith et al. | |
| 4,645,502 A | 2/1987 | Gale et al. | |
| 4,659,572 A | 4/1987 | Murray | |
| 4,675,009 A | 6/1987 | Hymes et al. | |
| 4,704,282 A | 11/1987 | Campbell et al. | |
| 4,710,191 A | 12/1987 | Kwiatek et al. | |
| 4,738,848 A | 4/1988 | Yoshida et al. | |
| 4,740,374 A | 4/1988 | Nakano et al. | |
| 4,854,610 A | 8/1989 | Kwiatek | |
| 4,854,995 A | 8/1989 | Kasper et al. | |
| 4,861,800 A | 8/1989 | Buyske | |
| 4,879,118 A | 11/1989 | Senuma et al. | |
| 4,880,416 A | 11/1989 | Horiuchi et al. | |
| 4,885,154 A | 12/1989 | Cormier et al. | |
| 4,915,102 A | 4/1990 | Kwiatek et al. | |
| 4,917,676 A | 4/1990 | Heiber et al. | |
| 4,917,895 A | 4/1990 | Lee et al. | |
| 4,954,343 A | 9/1990 | Hosaka et al. | |
| 4,994,267 A | 2/1991 | Sablotsky | |
| 5,064,422 A | 11/1991 | Wick | |
| 5,071,656 A | 12/1991 | Lee et al. | |
| 5,104,660 A | 4/1992 | Chvapil et al. | |
| 5,120,546 A | 6/1992 | Hansen et al. | |
| 5,123,900 A | 6/1992 | Wick | |
| 5,230,898 A | 7/1993 | Horstmann et al. | |
| 5,234,957 A | 8/1993 | Mantelle | |
| 5,240,932 A | 8/1993 | Morimoto et al. | |
| 5,300,291 A | 4/1994 | Sablotsky et al. | |
| 5,362,496 A | 11/1994 | Baker et al. | |
| 5,458,885 A | 10/1995 | Muller et al. | |
| 5,462,746 A | 10/1995 | Wolter et al. | |
| 5,474,783 A * | 12/1995 | Miranda et al. | 424/448 |
| 5,484,608 A | 1/1996 | Rudnic et al. | |
| 5,498,417 A | 3/1996 | Lhila et al. | |
| 5,618,555 A | 4/1997 | Tokuda et al. | |
| 5,762,952 A | 6/1998 | Barnhart et al. | |
| 5,972,376 A | 10/1999 | Sendl-Lang et al. | |
| 6,316,022 B1 | 11/2001 | Mantelle et al. | |
| 7,070,808 B2 * | 7/2006 | Govil et al. | 424/486 |
| 7,638,140 B2 | 12/2009 | Govil et al. | |
| 2001/0006628 A1 * | 7/2001 | Govil et al. | 424/78.31 |

FOREIGN PATENT DOCUMENTS

| | | |
|---|---|---|
| EP | 0 155 229 | 9/1985 |
| EP | 0 387 751 A2 | 9/1990 |
| EP | 0 509 761 A1 | 10/1992 |
| EP | 0 593 807 A1 | 4/1994 |
| JP | 2255612 | 10/1990 |
| JP | 4117323 | 4/1992 |
| JP | 6040888 | 2/1994 |
| JP | 7-138153 A | 5/1995 |
| JP | 8291069 | 11/1996 |
| WO | 89/09051 | 10/1989 |
| WO | 94/02123 | 2/1994 |
| WO | 95/01766 | 1/1995 |
| WO | 95/18603 | 7/1995 |
| WO | 96/40085 | 12/1996 |

* cited by examiner

OTHER PUBLICATIONS

Office Action from corresponding Japanese Applcation 10-179153, dated Jan. 28, 2009.
Office Action from corresponding Japanese Applcation 10-179153, dated Jan. 18, 2010.
European Examination Report for Application No. 04030946.0 dated Nov. 13, 2013.

*Primary Examiner* — Rebecca Prouty
*Assistant Examiner* — Danielle Sullivan
(74) *Attorney, Agent, or Firm* — Lerner, David, Littenberg, Krumholz & Mentlik, LLP

(57) ABSTRACT

Transdermal drug delivery patches and methods of their production are described. The patches can be made such that the accommodate highly plasticizing drugs such as selegiline and/or the use of protonated forms of various drugs.

11 Claims, 1 Drawing Sheet

US 8,846,093 B2

ADHESIVE MIXTURE FOR TRANSDERMAL DELIVERY OF HIGHLY PLASTICIZING DRUGS

CROSS REFERENCE TO RELATED APPLICATIONS

The present application is a continuation of U.S. application Ser. No. 12/286,236, filed on Sep. 29, 2008, now abandoned, which is a continuation of U.S. application Ser. No. 10/730,561, filed on Dec. 8, 2003, now U.S. Pat. No. 7,638,140, which is a divisional of U.S. application Ser. No. 09/754,909 filed on Jan. 5, 2001, now U.S. Pat. No. 7,070,808, which is a divisional of U.S. application Ser. No. 08/883,075 filed on Jun. 26, 1997, now U.S. Pat. No. 7,150,881, the disclosures of which are incorporated by reference herein.

The present invention relates to the field of pharmaceutical delivery devices and dosage forms and in particular, transdermal delivery vehicles as well as methods of making same.

BACKGROUND OF THE INVENTION

Most pharmaceutical formulations are available in salt forms. In fact, many formulations are only available in the form of a pharmaceutically acceptable salt. Salts have long been considered advantageous because of their high stability, ease of handling and formulation and generally high water solubility. Unfortunately, salt formulations do not tend to be useful in transdermal drug delivery systems. Because of the growing acceptance of such drug delivery systems by the general public, the inability to conveniently produce transdermal patches utilizing various pharmaceutical formulations is a great disadvantage.

There are many possible explanations for the general incompatibility of salt forms of drugs and transdermal performance. For example, protonated pharmaceutically active compounds (basic salts) are generally relatively high in polarity. It is known, however, that non-polar drugs, in general, are transmitted through the skin easily because of a high degree of compatibility with lipophilic layers of the skin. Highly polar substances such as salt forms of drugs and indeed some free forms of drugs, by virtue of their incompatibility with such lipophilic layers, are generally very slow in permeating skin.

One approach to forming a transdermal patch to overcome such problems was suggested in Yoshida et al., U.S. Pat. No. 4,738,848 and Nakano et al., U.S. Pat. No. 4,740,374. According to these patents, compounds such as diclofenac sodium and non-steroidal anti-inflammatory analgesic agents, when present in their salt forms, are difficult to dissolve into a pressure sensitive adhesive material having relatively high lipophilic properties. It is also difficult to maintain the active ingredient therein. If large amounts of drugs are added to the adhesive, in some cases, the drug cannot be dissolved or crystallization of the drug may occur. This makes it impossible to deliver a sufficient amount of the drug into the skin.

According to Yoshida et al. and Nakano et al., these difficulties can be overcome by concurrently using an organic acid during the formulation of the adhesive material. The organic acid apparently increases the solubility of the active ingredient in the pressure sensitive adhesive material and also increases the percutaneous absorption properties thereof. These references express their belief that the reason for the increased absorption properties is that the drug is converted to its free form having a higher oleophilicity (lipophilicity) resulting in the higher solubility of the drug.

Another approach was taken in Heiber et al., U.S. Pat. No. 4,917,676, which relates to a user-activated transdermal therapeutic system. The transdermal drug delivery system described therein includes separate compartments for various formulations in "pre-activated states". Just prior to use, the patient or other person applying the system allows the partitioned ingredients to commingle, thus activating the system. The user generally bursts a burstable barrier separating the two reservoirs. Then the therapeutic agent, usually in the form which must be altered for the desired transdermal delivery, and the activating substance combine and transform the therapeutic agent to a suitable species.

Inactive forms of therapeutic agents in accordance with Heiber et al. can include, for example, an acidic drug which, as an ionized species, penetrates skin to a slight degree, but in a free acid form, permeates freely through the skin. Activating substances may include pH regulators such as buffers, acids or bases.

Such transdermal systems, however, suffer from several disadvantages. First, they require a rather complex arrangement of two or more compartments separated by, for example, a burstable but otherwise nonpermeable material. In addition to the complexity of such a structure and the potential difficulties in separately filling and maintaining discretely the individual compartments, there is also the problem of premature bursting of the burstable layer and the premature intermingling of the various components. Clearly, the ability to manufacture a transdermal device wherein all of the necessary ingredients can be intermixed and intermingled from the start and added together to each and every cavity in a transdermal patch would be a great advantage. Finally, the Heiber et al. patent considers the complexities of forming a patch where the therapeutic and activity agents are mixed and maintained together at the time of manufacture or the subsequent storage stability problems attendant such a mixture.

Moreover, resolving the question of the physical state of a drug does not resolve all of the issues surrounding the production of transdermal patches from certain highly plasticizing drugs. In fact, providing these drugs in a free base form could actually raise additional problems. It comes as no surprise that a drug or solvent loaded into an adhesive system will have an effect on the adhesive properties of the resulting mixtures. In certain cases, with certain drugs, the effect on the hardness and tackiness of the resulting adhesive mixture is minimal. However, in certain other instances, drugs such as, for example, nitroglycerin or nicotine may act as plasticizers for many conventional adhesive systems. Plasticizing drugs such as these, can have a significant deleterious effect on the physical properties of the resulting adhesive matrix depending upon the type of drug, and the amount used. Generally, plasticizing drugs act to soften or disturb the structural integrity of the adhesive making it more fluid like and can, in certain cases, negatively effect the degree of adhesivity.

A number of companies have introduced either high molecular weight or highly crosslinked adhesive systems. It is known that these systems can generally be used almost interchangeably with plasticizing drugs. Typical examples of such adhesives include, without limitation, GELVA 737, GELVA 2655, and GELVA 1753 self crosslinkable acrylic adhesives from Monsanto's Chemical Group, 730 Worcester Street, Springfield, Mass. 01151 and DUROTAK 87-2516, DUROTAK 87-2194 and DUROTAK 87-2852 self crosslinkable acrylic adhesives available from National Starch and Chemical Company, 10 Finderne Ave., P.O. Box 6500, Bridgewater, N.J. 08807-0500. All of these crosslinked adhesives find wide spread use in the pharmaceutical industry in the formulation of transdermal drug delivery systems. When liquid, lipophilic drugs are added to these adhesives at amounts of between 30 and about 40% the resulting material would generally not suffer deterioration in physical properties so as to render many of these acrylic based adhesives unusable. While many of these adhesives are virtually interchangeable, of course, some combinations of a specific drug and a specific adhesive may provide marginally better properties.

When the inventors attempted to construct a transdermal delivery vehicle for selegiline, a particularly highly plasticizing drug, they too expected that selegiline patches produced with any of the foregoing class of adhesives could be accomplished without a problem. This was particularly true as loading levels were anticipated at only between about 10 and about 20%; not particularly challenging for these adhesives.

As illustrated in Table 1, when mixtures of selegiline (15 wt %) and various adhesive materials were tested using conventional performance tests, they all demonstrated comparable and generally acceptable results.

TABLE 1

POLKEN TACK OF VARIOUS TRANSDERMAL ADHESIVES WITH 15% SELEGILINE

| ADHESIVE | POLKEN TACK |
| --- | --- |
| GELVA 1753 | 346 |
| DUROTAK 87-2194 | 453 |
| GELVA 737 | 333 |
| DUROTAK 87-2516 | 286 |

Yet when these formulations were tried on skin, the results were quite surprising. While some of the formulations worked, others unexplainably exhibited significant cohesive failure whereby adhesive remained on the skin after a transdermal patch was peeled-away. The disparity in the results obtained between conventional "bench-top" testing and actual field application was truly discouraging. It essentially placed a whole host of established tests in a highly compromised state.

The inventors were also taken aback by the degree of disparity observed. When they formulated a selegiline containing transdermal patch with, for example, DUROTAK 87-2194, those patches exhibited cohesive failure and adhesive transfer. Formulations made with GELVA 2655 exhibited total adhesive failure. Neither result could have been predicted based on results such at that reported in Table 1. This problem was only amplified by the use of other traditional tests such as a measure of shear strength. As shown in Table 1A, a number of formulations including selegiline were measured in terms of shear strength.

TABLE 1A

SHEAR STRENGTH OF DIFFERENT ADHESIVE SYSTEMS WITH SELEGILINE BASE

| ADHESIVE | SHEAR (MIN) | SELEGILINE |
| --- | --- | --- |
| GELVA 737 | 4.31 | 13% |
| GELVA 788 | 3.1 | 13% |
| DUROTAK 87-2516 | 1174 | 13% |
| DUROTAK 87-2194 | 36 | 13% |
| GELVA 1753 | 1440 | 4% |
| GELVA 1753 | 1440 | 8% |
| GELVA 1753 | 1440 | 13% |

Typically, shear values of greater than about a half an hour to one hour would be considered acceptable adhesive systems. As one can see from Table 1A, GELVA 1753 produced relatively high shear rates, which should indicate an acceptable adhesive system. However, DUROTAK 87-2516 also exhibited acceptable shear, and the formulations made from this adhesive were totally unacceptable when applied to skin. In addition, selegiline with 10% propylene glycol as a solvent, provided shear values of greater than 800 minutes when formulated with GELVA 1753. However, while such results are generally indicative of good adhesion characteristics, this particular formulation exhibited very poor adhesion.

Much to their dismay, the inventors discovered that with a certain class of particularly highly plasticizing drugs, only selected adhesives would work. They also found that, based on the state of the art, they could not predict which adhesives would work and which would not.

SUMMARY OF THE INVENTION

One aspect of the present invention is the creation of a free base material in an adhesive and or in a transdermal patch, or just prior to mixing with the adhesive. The result is the creation of a transdermal patch including the converted free base of the drug material. Another aspect of the present invention involves the creation of certain transdermal formulations which include a highly plasticizing drug, in free base form, whether the free base was created in situ or not.

Therefore, in accordance with one aspect of the present invention, a method of producing an adhesive formulation for a therapeutic drug delivery patch adapted for the percutaneous or transdermal delivery of a drug is provided. The method includes the step of providing a pharmaceutically active agent in protonated form, whose corresponding free base has a given $pK_b$ which ranges from between about 4.75 and about 11. Then, the protonated pharmaceutically active agent is dissolved in a nonaqueous solvent, the nonaqueous solvent being capable of dissolving the pharmaceutically active agent in both a protonated and unprotonated forms.

The dissolved pharmaceutically active agent is reacted with a biocompatible deprotonating agent which can substantially deprotonate the pharmaceutically active agent without causing irritation upon prolonged exposure to the skin. The deprotonated agent will have a $pK_b$ which is at least about 0.75 lower than the $pK_b$ of the pharmaceutically active agent. The deprotonated agent thereby becomes protonated. The deprotonating agent may be selected and apportioned such that some excess of unreacted deprotonating agent remains. Finally, the deprotonated pharmaceutically active agent is incorporated into an adhesive material. In a particularly preferred embodiment, these methods also include the steps of separating at least a portion of the now protonated deprotonating agent from the mixture of deprotonated pharmaceutically active agent, solvent and protonated deprotonating agent prior to incorporating the pharmaceutically active agent into the adhesive material. The now protonated deprotonating agent can also be removed after it has been added to an adhesive as well.

In addition, in accordance with another aspect of the present invention, it is possible to actually undertake the deprotonation of the protonated pharmaceutically active agent, in situ, within the adhesive material. Moreover, in accordance with still another aspect of the present invention, it is possible to construct a patch in such a way that the protonated pharmaceutically active agent and the deprotonating agent are disposed in discrete but adjacent dry layers.

Over time, the deprotonation reaction occurs in situ such that the resulting patch includes a deprotonated pharmaceutically active agent or drug which is capable of enhanced skin penetration.

Of course, the designing of an acceptable adhesive formulation for incorporation into a transdermal patch, one which allows for the conversion of a protonated drug to its free form and can accommodate the presence of deprotonating agent, can be extremely demanding. For example, many polymer based adhesive systems are fairly incompatible with the drug in its salt form. Finding a way of introducing the salt to the adhesive must therefore be developed. In doing so, however, it must be realized that after conversion the resulting free form of the drug must also be compatible with the adhesive. Similarly, a patch in accordance with the present invention or an adhesive formulation in accordance herewith would require the incorporation of some agent which would convert the protonated form of the drug, such as a protonated amine form, to its free form. This deprotonating agent, like the therapeutic pharmaceutically active agent itself, will undergo transformation. It is important, therefore, to ensure that both the deprotonating agent, and that agent in its later protonated form, are also compatible with the adhesive base in terms of stability. This means finding a system where either the protonated deprotonating agent will remain dissolved in the solvent/adhesive material system, or the crystallized protonated deprotonating agent will not have an adverse effect on the transdermal device or the patient.

When highly plasticizing drugs are being formulated into transdermal patches, the interaction of the drug and the adhesive system can become even more complex. Not only must the system be able to accommodate the various states of the drug and deprotonating agent, but they must also meet some rather unique criteria for the use of highly plasticizing drugs as well.

Surprisingly, formulations which address and balance all of the often competing requirements of converting a protonated drug to its free form, in situ, in a percutaneous dosage form or transdermal patch and accommodating highly plasticizing drugs have been developed. The resulting patches have long term storage stability, reliable release profiles, high levels of skin permeation and, best of all, are easy and economical to manufacture. Additionally, it has been discovered that, by the practice of the present invention, it may be possible to tailor the rate of release of the free form of the drug, and thereby its permeation through the skin, by controlling the rate of reaction of the various reactive components within the patch.

In accordance with a particularly preferred aspect of the present invention there are provided methods of producing transdermal delivery vehicles for highly plasticizing drugs. These methods involve providing between about 97% and about 65%, by weight, of a very specific class of acrylic polymeric adhesives. This acrylic polymeric adhesive includes between about 40% and about 90% by weight of a $C_4$-$C_{12}$ alkyl acrylate, between about 10% and about 40% by weight of a $C_1$-$C_4$ alkyl acrylate hardening monomer; between about 1% and about 15% by weight of a functionalizing monomer which facilities crosslinking; and, in many instances, a crosslinking agent. The acrylic polymeric adhesive is mixed with a highly plasticizing drug provided in an amount of between about 3% and about 35% by weight based on the dry weight of the mixture. The therapeutic adhesive formulations and transdermal patches using same are also contemplated.

Most preferably, the highly plasticizing drug is selegiline which is provided in an amount of between about 3 and about 18% by weight, based on the dried mixture. Also preferably, the only solvents used in the production of therapeutic adhesive formulations including a highly plasticizing drug provided in a free base form are relatively high volatility solvents, such as ethanol, which will be removed upon drying as well as those solvents found in the acrylic polymeric adhesive which prevent in situ cross-linking and maintain the adhesive in liquid form until removed. Solvents which will remain after drying, such as propylene glycol used for deprotonation are preferably not used in these adhesive formulations.

After observing the unexpected failure of certain highly crosslinked acrylic based adhesives to maintain their advantageous properties following the incorporation of moderately low doses of selegiline, the inventors discovered that a relatively small class of acrylic based adhesive formulations can be used with particularly aggressively plasticizing drugs. The reasons why these particular acrylic based adhesives work with certain highly plasticizing drugs and why other very closely related adhesive formulations fail is not fully appreciated. However, from amongst the numerous commercially available adhesive formulations of which those of ordinary skill in the art traditionally look to solve these sorts of problems, only a few have been identified as being useful in these cases, and these adhesives do have some common properties.

In another preferred aspect of the present invention, there is provided a method of producing a therapeutic adhesive formulation for use in a transdermal patch. The method includes the step of selecting an acrylic polymeric adhesive which is suitable for use with highly plasticizing drugs. This decision is not based upon the bench-tested properties of the adhesive but rather upon it's content of between about 40% and about 90% of a $C_4$-$C_{12}$ alkyl acrylate and between about 10% and about 40% by weight of a $C_1$-$C_4$ alkyl acrylate hardening monomer. Once the acrylic polymeric adhesive is selected, it is mixed with the highly plasticizing drug in an amount of between about 3% and about 35% by weight based on the weight of said mixture and on a liquid basis.

Often the selection process for the adhesive also involves consideration of the content of a functionalizing monomer which facilitates crosslinking; and/or a crosslinking agent. This method may therefore also include the step of crosslinking the acrylic polymeric adhesive to form a matrix capable of controlling the release of the highly plasticizing drug when used in a transdermal patch and applied to the skin of a patient. The proper selection and formulation of this adhesive material will result in a transdermal patch and which will not ooze, suffer from adhesive failure, fall off of a patient prematurely or be difficult to remove when necessary.

Applicants have also discovered that the traditional benchtop methods of gauging the performance of such adhesives are unreliable with particularly highly plasticizing drugs like selegiline. Therefore while tests like shear strength, peel tests from a steel plate and tack tests may eliminate certain candidates, they will not reliably identify successful candidates. Instead, it was discovered that the acrylic polymeric adhesives that worked the best in these application all have similar compositions. Generally, they include a $C_4$-$C_{12}$ alkyl acrylate, a lower alkyl acrylate ($C_1$-$C_4$) hardening monomer such as methyl acrylate and a functionalizing monomer such as acrylic acid which facilities crosslinking. A crosslinking agent is also often useful.

DETAILED DESCRIPTION

Figure 1:
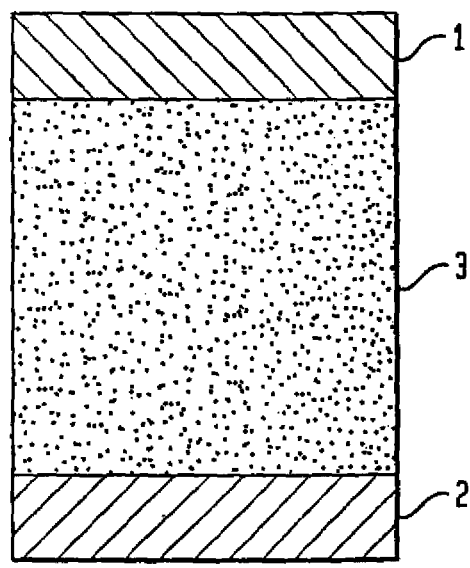
FIG. 1 is a side planar view of a drug delivery patch in accordance with the present invention.

The terms pharmaceutically active agent and drug are used synonymously, and these terms include any drug or biologically active substance which is available in protonated form. These pharmaceutically active agents must be capable of transdermal application and must be susceptible to inclusion in a patch in accordance with the present invention, both in protonated and nonprotonated forms. Additionally, the drug must be compatible with the other ingredients that are components of the therapeutic adhesive formulation. Generally, the content of the formulation will be tailored around the pharmaceutically active agent. However, if the pharmaceutically active agent cannot be stored in contact with, for example, any of the biocompatible deprotonating agents in accordance with the present invention, then that drug is not a candidate for use in some of the therapeutic adhesive formulations discussed herein. That is, of course, unless the drug can be provided in a free base form without any of the deprotonating agent. In addition, the drug should not cause irritation to the skin of the patient in either protonated or deprotonated form. Similarly, the drug should be susceptible of deprotonation by an agent which itself will not cause any irritation, unless the drug will be provided as a free base. This will further limit and define the class of the drugs capable of use in accordance with the present invention.

Without limitation, pharmaceutically active agents in accordance with the present invention may include selegiline-HCl, propranolol-HCl, ketorolac-HCl, buprenorphine-HCl, scopolamine-HCl, terbutaline-HCl, clonidine-HCl, morphine-HCl, terazosin-HCl, prazosine-HCl, diliazem-HCl, verapamil-HCl and Ciprofloxacin-HCl. The amount of the pharmaceutically active agent will vary widely. Some drugs are active in dosages of a few milligrams per day while others may require thousands of milligrams per day. However, in general, the pharmaceutically active agents in accordance with the present invention are provided in an amount which ranges from between about 0.1 to about 45 percent by weight based on the total formulation. More preferably, the amount of drug ranges from between about 2 to about 20 percent by weight based on the weight of the total formulation.

The pharmaceutically active agent has a $pK_b$ of at least about 4.5-5.0 and no more than about 11-11.5. The deprotonating agent should have a $pK_b$ of at least about 3.5-4.0 and no more than about 10.0-10.5. References to the $pK_b$ of the pharmaceutically active agent are always to the $pK_b$ of the free base form of the drug. In addition, the $pK_b$ of the deprotonating agent should be at least about 0.75, preferably 1.0 and more preferably 2.0 less than the $pK_b$ of the drug.

The term highly plasticizing drug generally means, a pharmaceutical or biologically active agent having a low molecular weight (under 300 MW), being liquid at normal process temperatures, and of an oily or lipophilic nature such that it fluidizes the adhesive and would cause viscous cold flow at adhesive during normal stage. The result would be ooziness and eventually, cohesive failure or splitting of the adhesive material. If the highly plasticizing drug can be provided as a free base, then its $pK_b$ will not be an issue. Typically, the highly plasticizing drug in accordance with the present invention would be provided in an amount ranging from between about 3% to about 35% based on the weight of the finished adhesive and drug mixture (dry weight). More preferably, the amount of drug will range from between about 3% to about 25%. Most preferably, the amount will range from between about 3% and about 18%. Preferred particularly highly plasticizing drugs in accordance with the present invention include: selegiline, fluoxetine, Des-methyl selegiline, tetracaine and chlorpheniramine.

As used herein, a therapeutic adhesive formulation includes an adhesive formulation which can be utilized as part of a percutaneous or transdermal drug delivery patch or the like. The therapeutic adhesive formulation may be provided as one or more thin adhesive layers in a patch, can be placed in a recess or cavity within a patch as a monolithic structure or as a relatively viscous gel-like substance.

The therapeutic adhesive formulation in accordance with the present invention generally includes at least two components: at least one adhesive formulation and a pharmaceutically active agent. If the drug used is in a protonated form, then it will be necessary to include a solvent capable of dissolving the drug, in both protonated and deprotonated form. Such solvents may remain in the formulation after drying. If the drug used is a highly plasticizing drug provided in protonated form, then the amount of this type of solvent should be minimized as it may affect the adhesion characteristics of the resulting therapeutic adhesive formulation. If the highly plasticizing drug is provided as a free base, then there is most often no need for such a solvent at all. In fact, under such circumstances, it is desirable to avoid using a low-volatility solvent which will not be driven off during drying, if possible. This lowers the amount of drying required which reduces the loss of drug. It also reduces the cost of the formulations and eliminates a potential source of adhesion problems. In cases where a protonated form of the drug is used, the therapeutic adhesive formulation also includes at least some amount of a biocompatible deprotonating agent. Each of these components, as well as any others that may be used such as dyes, permeation enhancers, crosslinkers, adhesion promoters, gelling agents, crystallization inhibitors, anti-inflammatory agents and the like are mixed together in a generally homogeneous mixture. This mixture is then formed into a film, block or where appropriate, poured into a mold, or poured directly into the cavity or recess of a patch.

While, as discussed in late passages, the adhesive formulations useful with highly plasticizing drugs are defined more restrictively, the adhesive formulation useful in accordance with the present invention may include any adhesive useful in accordance with the creation of transdermal patches. Broadly, these include acrylics, silicones, polyisoalkylenes, rubbers, vinyl acetates, polyisobutylene rubber, polybutadiene, styrene-butadiene (or isoprene)-styrene block copolymer rubber, acrylic rubber and natural rubber; vinyl-based high molecular weight materials such as polyvinyl alkyl ether, polyvinyl acetate, a partially saponified product of polyvinyl acetate, polyvinyl alcohol and polyvinyl pyrrolidone; cellulose derivatives such as methyl cellulose, carboxylmethyl cellulose and hydroxypropyl cellulose; polysaccharides such as pullulan, dextrin and agar; polyurethane elastomers; and polyester elastomers. Of course, the adhesives must be biocompatible and nonirritating. They must also allow for a patch to adhere firmly to the skin of a patient in need of treatment by a patch but not be so adhesive so as to injure the patient as the patch is removed. It is also important that the adhesive be selected such that it is compatible with the other components of the therapeutic adhesive formulation of the present invention. It has been found that, as a group, the acrylic adhesives are particularly useful and compatible in this regard and therefore, it is preferred that the adhesive used be acrylic based. More specifically, acrylic adhesives in accordance with the present invention may preferably be (meth)acrylic acid such as butyl(meth)acrylate, pentyl(meth)

acrylate, hexyl(meth)acrylate, heptyl(meth)acrylate, octyl(meth)acrylate, nonyl(meth)acrylate, decyl(meth)acrylate, undecyl(meth)acrylate, dodecyl(meth)acrylate, and tridecyl(meth)acrylate, and copolymers of at least one of the above esters and other monomers copolymerizable therewith.

Examples of the copolymerizable monomer include carboxyl group-containing monomers such as (meth)acrylic acid, itaconic acid, crotonic acid, maleic acid, maleic anhydride and fumaric acid; sulfoxyl group-containing monomers such as styrenesulfonic acid, arylsulfonic acid, sulfopropyl acrylate, (meth)acryloyloxynaphthalenesulfonic acid, acrylamidomethylpropanesulfonic acid and acryloyloxybenzenesulfonic acid; hydroxyl group-containing monomers such as hydroxyethyl(meth)acrylate and hydroxypropyl(meth)acrylate; amide group-containing acrylic monomers such as (meth)acrylamide, dimethyl(meth)acrylamide, N-butylacrylamide, tetramethylbutylacrylamide and N-methylol(meth)acrylamide; alkylaminoalkyl group-containing acrylic monomers such as aminoethyl(meth)acrylate, dimethylaminoethyl(meth)acrylate, diethylaminoethyl(meth)acrylate and tertbutyl(meth)acrylate; alkyl esters of acrylic acid containing an ether bond in the molecule thereof such as methoxyethyl(meth)acrylate, ethoxyethyl(meth)acrylate, butoxyethyl(meth)acrylate, tetrahydrofurfuryl(meth)acrylate, methoxyethylene glycol(meth)acrylate, methoxydiethylene glycol(meth)acrylate, methoxypolyethylene glycol(meth)acrylate and methoxypolypropylene glycol(meth)acrylate; vinyl monomers such as N-(meth)acryloylamino acid; functional monomers such as acrylic monomers such as urethane, urea or isocyanate ester of acrylic acid; and vinyl monomers such as (meth)acrylonitrile, vinyl acetate, vinyl propionate, vinyl pyrrolidone, vinyl pyridine, vinyl pyrazine, vinyl piperadine, vinyl piperidone, vinyl pyrimidine, vinyl pyrrole, vinyl imidazole, vinyl caprolactam, vinyl oxazole, vinyl thiazole, vinyl morpholine, styrene, a-methylstyrene and bis(N, N'-dimethylaminoethyl) maleate.

The above alkyl esters of (meth)acrylic acid and copolymerizable monomers include isomers in which the alkyl portion is straight or branched, and isomers and derivatives in which the position of substituents is different.

It is desirable from a standpoint of the balance between adhesive properties to the skin and cohesion that the ratio of the alkyl ester of (meth)acrylic acid to the copolymerizable monomer in the acrylic pressure-sensitive adhesive material is 50:50 to 99:1 by weight. When alkyl esters of (meth)acrylic acid containing an ether bond in the molecule thereof are used from the standpoint of the low skin irritating properties, it is desirable that the ratio of the alkyl ester of (meth)acrylic acid/the alkyl ester of (meth)acrylic and containing an ether bond in the molecule/the other copolymerizable monomer is 40 to 80/59 to 10/1 to 40.

It is preferred that the adhesive formulations be subjected to suitable chemical crosslinking treatment (e.g., copolymerization of crosslinkable monomers and addition of a crosslinking agent) or physical crosslinking treatment (e.g., irradiation with ultraviolet rays and ionizing radiations such as electron beam).

In accordance with the present invention, the amount of adhesive generally utilized ranges from between about 30 to about 85 percent by weight based on the total weight of the resulting formulation. Preferably, the amount of adhesive used ranges from between about 45 to about 75 percent by weight based on the total weight of the formulation.

When the transdermal patch in accordance with the present invention will be used to deliver highly plasticizing drugs, a more specific group of acrylic based adhesives has been found to be useful. These are identified herein as acrylic polymeric adhesives.

Acrylic polymeric adhesives in accordance with this aspect of the present invention include between about 40% and about 90% of a $C_4$-$C_{12}$ alkyl acrylate as the principal monomeric component. Any alkyl acrylate having between 4 and 12 carbons which has been used for the formulation of transdermal adhesives can be used, although, of course, other acrylates are also contemplated. Traditional $C_4$-$C_{12}$ alkyl acrylates useful in accordance with the present invention include, for example, 2-ethylhexyl acrylate, butyl acrylate, n-decyl, n-nonyl, 2 ethyoctyl, isooctyl and dodecyl-acrylate Generally, the $C_4$-$C_{12}$ alkyl acrylate in accordance with the present invention will be used in a matter of between about 40 and about 90% based on the weight of the finished adhesive material. More preferably, however, the amount of the $C_4$-$C_{12}$ alkyl acrylate will range from between about 60% to about 80% by weight, based on the weight of the adhesive.

The properties of the acrylic polymeric adhesive can be dramatically altered depending upon whether or not a hardening monomer is used and the type of hardening monomer used. It has been found that the use of between about 10% and about 40% by weight of a $C_1$-$C_4$ alkyl acrylate hardening monomer, in combination with the $C_4$-$C_{12}$ alkyl acrylate, is the key to providing an acrylic polymeric adhesive system capable of providing desirable therapeutic delivery, as well as structural integrity, for transdermal application of highly plasticizing drugs as discussed herein. Examples of $C_1$-$C_4$ alkyl acrylate hardening monomers useful in accordance with the present invention include methyl acrylate, methyl methacrylate, ethylacrylate, ethyl methacrylate, hydroxyethyl acrylate and hydroxy propyl methacrylate. More preferably, the amount of $C_1$-$C_4$ alkyl acrylate hardening monomer useful in accordance with the present invention ranges from between about 15% to about 30% based on the weight of the adhesive.

It has been discovered that the attributes of the acrylic polymeric adhesive when used with highly plasticizing drugs are largely a function of the $C_4$-$C_{12}$ alkyl acrylate and the hardening monomer selected. The compositions of various commercially available transdermal adhesives are provided below in Table 2.

TABLE 2

| | COMPOSITIONS OF VARIOUS TRANSDERMAL ADHESIVES | | | | | |
|---|---|---|---|---|---|---|
| | GELVA 788 | GELVA 737 | DUROTAK 2194 | GELVA 753 | DUROTAK 2516 | DUROTAK 2852 |
| 2-Ethyl Hexyl Acrylate | 67 | 67 | 75 | 61 | 70 | 65 |
| Methyl Acrylate | | | | 33 | | 27.5 |
| Vinyl Acetate | 28 | 28 | 20 | | 25 | |

TABLE 2-continued

COMPOSITIONS OF VARIOUS TRANSDERMAL ADHESIVES

| | GELVA 788 | GELVA 737 | DUROTAK 2194 | GELVA 753 | DUROTAK 2516 | DUROTAK 2852 |
|---|---|---|---|---|---|---|
| Acrylic Acid | | | 5 | 6 | | 7.5 |
| Hydroxy Ethylacrylate | 5 | 5 | | | 5 | |
| Glycidyl Methacrylate | <0.5 | <0.5 | | <0.1 | Yes | |
| X-Linker | No | Butyl Titinate | Aluminum Isopropoxide | Aluminum Isopropoxide | Polybutyl Titinate | Aluminum |

These materials all have similar amounts of 2-ethyl hexyl acrylate (A $C_4$-$C_{12}$ alkyl acrylate) and similar amounts of a functionalizing monomer which facilitates crosslinking. (Three of the formulations have between about 6 and about 7.5% acrylic acid, and the remaining formulations have about 5% hydroxy thylacrylate.) Two of the compositions, both of which have been found to be effective in accordance with the present invention, GELVA 1753 and DUROTAK 87-2852 each contain a hardening monomer which is methyl acrylate. The remaining formulations contain vinyl acetate as the hardening monomer. Vinyl acetate is a widely employed monomer for this purpose.

In accordance with the present invention, it is also desirable to use a functionalizing monomer which facilitates crosslinking. Functionalizing monomers provide functional groups for crosslinking. Such functionalizing monomers are well known in the art and include, for example, acrylic acid, hydroxy ethylacrylate, methacrylic acid, and acrylamide. It should be noted, however, that when using an acrylate hardening monomer in an acid form, it is preferred to use a functionalizing monomer, such as acrylic acid, whereas, where the hardening monomer is an alcohol, compounds such as hydroxy thylacrylate should be chosen. Functionalizing monomers are generally provided in the range and between about 1% and about 20%.

It is also desirable to include a crosslinking agent. Crosslinking agents can include butyl titanate, polybutyl titanate, aluminum zinc acetate and other multivalent metals, methylol ureas and melamines Generally the crosslinking agent is provided in an amount of between about 0.005 and about 2% the adhesive.

Crosslinking can be effected in many ways depending upon a number of factors. Most importantly, crosslinking depends upon the mode of action of the crosslinking agent. Most of the acrylic polymeric adhesive formulations commercially available use crosslinking agents which will be activated upon the drying of the formulation. It is not the heat which activates these agents but rather the removal of the solvent by, for example, evaporation or drying. Drying to remove these solvents can by done under completely conventional conditions such as 100 to 140° F. It should be noted that certain formulations are commercially available without crosslinkers. For example, GELVA 1430 is identical to GELVA 1753 except that it does not include a crosslinker. This allows one to accommodate situations where no crosslinking is needed (such as when very low concentrations of drug are used) or to custom select a crosslinker that has a different mode of action.

It should also be noted that the solvents found in the adhesives which maintain the liquid form of the adhesive and generally prevent the activation of the crosslinkers are not to be confused with the low-volatility solvents which can be added as part of the dissolution system for patches using a protonated drug. Solvents normally found in commercial adhesive formulations, solvents included merely to prevent premature crosslinking, or relatively high volatility solvents such as ethanol, used only during mixing and processing, which are evaporated during drying are generally not a problem with regard to the properties of the adhesives.

As shown in Table 3, quite unexpectedly, the properties of the resulting adhesive vary greatly with relatively minor variations and the relative amounts of the various ingredients. It is clear, therefore, that the unique combinations of monomers is primarily responsible for dictating whether or not a particular adhesive formulation will be successful with a highly plasticizing drug discussed herein.

TABLE 3

EFFECT OF SELEGILINE AND PLASTICIZER COMBINATION ON VARIOUS PHYSICAL PROPERTIES OF VARIOUS ADHESIVES

| ADHESIVE | PLASTI-CIZER | SELEGI-LINE | PEL FROM SS (gm/in) | PHYSICAL OBSERVATIONS |
|---|---|---|---|---|
| GELVA 1753 | 0 | ~18% | — | |
| | 0 | ~15% | 1110 | No Adhesive Transfer |
| | 0 | ~10% | 933 | Transfer |
| | 10% PG | 8% | 527 | No Oozing |
| DUROTAK 87-2194 | 10% PG | 8% | 2217 | Adhesive Transfer (Cohesive Failure) |
| GELVA 788 | 10% PG | 8% | 1267 | Adhesive Transfer |
| DUROTAK 87-2516 | 10% PG | 8% | 960 | Adhesive Transfer |
| GELVA 2655 | 0 | 18% | — | Total Adhesive Failure |
| DUROTAK 87-2852 | 0 | 12% | — | No Adhesive Transfer |
| | 0 | 18% | — | No Oozing Somewhat Soft |

Only those adhesive/drug formulations which included a $C_1$-$C_4$ alkyl acrylate hardening monomer as discussed above provided the necessary performance in terms of adhesive transfer and oozing to allow it to be useful for transdermal applications without adhesive transfer on skin.

It is interesting to note from Table 3 that GELVA 1753 provided acceptable results in terms of adhesive transfer and oozing. However, the formulation which included 10% propylene glycol ("PG"), a relatively low-volatility solvent used in systems involving protonated drugs, also exhibited relatively poor adhesive characteristics. It has been found that the use of these types of solvent only amplifies the plasticizing effects of highly plasticizing drugs. Therefore, when a free base form of a highly plasticizing drug is used, it is desirable to reduce, if not eliminate, the use of such low-volatility solvents. Of course, this has other processing advantages, as it reduces costs, exposes a patient to fewer chemicals, reduces chemical waste and reduces process time, both in terms of preparation and in terms of drying the formulation.

Other acrylic polymeric adhesives containing the proper combination of ingredients include GELVA 2873 (similar to 1753, but without residual monomers) and DUROTAK 87-2852.

When the pharmaceutically active agent used is a protonated form, it must be converted to its free form, before, during or after being mixed with the adhesive thereby rendering it more readily permeable through the skin of a patient. Protonated forms of pharmaceutically active agents, including highly plasticizing drugs, are generally incompatible with the adhesive materials described above. However, the present inventor has found that this problem can be overcome by dissolving the usually solid salt in a nonaqueous solvent which is capable of maintaining the pharmaceutically active agent in both its protonated and nonprotonated form. Again, there are trade-offs based on the use of this type of solvent and highly plasticizing drugs, particularly if the solvent used has a relatively low-volatility such as PG.

In accordance with the present invention, the nonaqueous solvent is preferably an alcohol. Alcohols in accordance with the present invention can include monoalcohols, such as ethanol, propanol, isopropanol, butanol, and tertbutyl alcohol. The alcohol may also be a generally low molecular weight polyols, i.e., glycols such as propylene glycol and polyalkylene glycol having an average molecular weight of less than about 400. For example, the nonaqueous solvent may be polyethylene glycol having an average molecular weight of between about 200 and about 400.

Most preferably, a nonaqueous solvent in accordance with the present invention is a normal short chain polyol of between about 2 and about 4 carbons in length. Such polyols may include 1,4 butanediol, glycerol, ethylene glycol, propylene glycol, and the like. Also useful in accordance with the present invention are acetates such as, for example, ethyl acetate, cellulose acetate, vinyl acetate and the like.

It is important that the nonaqueous solvents not only be compatible with the adhesive material and the pharmaceutically active agent, both in its protonated and nonprotonated forms, but also that it be compatible with the biocompatible deprotonating agent as well. Moreover, the nonaqueous solvent must be compatible with the biocompatible deprotonating agent in both its protonated and nonprotonated forms. The nonaqueous solvent must also be biocompatible such that it will not cause irritation or discomfort when in contact with the skin of a patient.

The amount of nonaqueous solvent used in accordance with the present invention must be sufficient to completely dissolve both the pharmaceutically active agent and the biocompatible deprotonating agent. Thus the amount may vary widely with the amount of each such ingredient used. However, in general, the therapeutic adhesive formulation in accordance with the present invention may include an amount of nonaqueous solvent ranging from between about 5 to about 30 percent by weight based on the total weight of the formulation. More preferably, the nonaqueous solvent is provided in an amount of between about 10 and about 20 percent by weight based on the weight of the total formulation.

When the pharmaceutically active agent is a highly plasticizing drug, then it may be necessary to reduce the amount of nonaqueous solvent used, particularly those which do not evaporate during drying. As previously noted, certain solvents can accentuate the highly plasticizing nature of the drug, or can reduce the adhesive characteristics of the resulting patch, if they remain. In such cases, it is preferable to use only solvents which will volatilize or evaporate during drying and to use other solvents in amounts of less than about 10% by weight. Preferably as little solvent is used as possible. The exact amount of solvent useful in accordance with this aspect of the invention, will vary considerably, depending upon the exact acrylic polymeric adhesive system selected, the specific highly plasticizing drug used and the amount of the highly plasticizing drug provided. Generally though, the more highly plasticizing the drug, and the greater the overall content, the lower the amount of non-volatile solvent which can be accommodated before yielding undesirable properties.

Of course, during the normal drying process, at temperatures ranging from 100-200° F., any solvents in the system, whether provided as part of the adhesive or added or evaporated or dried. The high-volatility solvents are driven off and lower-volatility solvents are dried. However, this process can also cause the loss of drug, particularly when using highly plasticizing drugs. Therefore, to provide a formulation or patch containing between about 3% and about 35% dry as desired, one might need to add as much as 100% (70% by weight) additional drug to the adhesive prior to drying. The amount of additional drug will vary with the drug or drugs used, the type of adhesive and the amount and types of solvents and the drying conditions. By lowering drying temperatures and eliminating additional solvents (those not found in the commercial adhesive) the amount of drug lost can be reduced. By consistent formulation and drying conditions, it is possible to determine the amount of drug lost so as to provide full compensation therefore. The result will be patches having the desired amount of drug.

Finally, the biocompatible deprotonating agent provided must be strong enough to substantially deprotonate the pharmaceutically active agent, but must not be so aggressive so as to cause irritation upon prolonged exposure to the skin. The biocompatible deprotonating agent must also be selected so that it is storage compatible with the drug and soluble, in both protonated and nonprotonated forms, in both the adhesive material and the nonaqueous solvent.

In order to be strong enough to substantially deprotonate the pharmaceutically active agent, it should be generally understood that the biocompatible deprotonating agent should have a $pK_b$ which is at least 0.75 lower than the $pK_b$ of the deprotonated form of the pharmaceutically active agent. More preferably, the $pK_b$ differential is 1.0 or 2.0, or even greater. For example, if the active drug in free form has a $pK_b$ of about 9.0, then the deprotonating agent in accordance with the present invention should have a $pK_b$ of about 8.25 and, more preferably 8 or less. At the same time, the biocompatible deprotonating agent should not be so aggressive so as to cause irritation upon prolonged exposure to skin. Thus the $pK_b$ of the deprotonating agent should not be under at least about 3.5-4.0 or over about 10.0-10.25. More, preferably, the $pK_b$ of the drugs (in deprotonated form) will range from between about 5 and about 11 and the $pK_b$ of the deprotonating agents will range from between 4 and about 10. Of course, in some cases, it may be possible to use a lower $pK_b$, but the risk of irritation grows accordingly.

By prolonged exposure to skin, it should be understood that certain patches may only be in contact with skin for a matter of hours, while others may be left on for a matter of days. In the context of longer term patches left in contact with the skin for greater than about 8 hours, the meaning of the term should be readily apparent. However, as to shorter exposure patches, the term prolonged exposure to the skin contemplates irritation caused by repeated administration of a patch to the same area of skin.

The biocompatible deprotonating agent in accordance with the present invention may be any compound which is capable of deprotonating the drug, and which is compatible with the formulations in the present invention. Preferably, the biocompatible deprotonating agent can be polymeric imines, aromatic imines, alkanol imines, polymeric amines, aromatic amines, alkanolamines, alkyl-aryl amines, and the like.

Particularly preferred deprotonating agents in accordance with the present invention include alkanolamines such as, for example, triethanolamine, diethanolamine, ethanolamine, propanolamine, ammonia and the like. Other biocompatible deprotonating agents in accordance with the present invention include polymeric imines such as, for example, polyethylene imine ("PEI"), polydimethylaminoethyl methacrylate such as Eudragit E100 from Rohm Pharmacy and polyacryloamin. PEI is a particularly interesting biocompatible deprotonating agent as it tends to form a sphere or cage which may encapsulate or entrap some of the pharmaceutically active agent. The rate of reaction between the PEI and protonated drugs will depend largely upon the molecular weight of the PEI. Therefore, by tailoring the size of the PEI, it may be possible to control, at least to some degree, the rate of deprotonation.

It is also possible to use a second drug as a deprotonating agent. For example, if drug X has a $pK_b$ of 9 and drug Y has a $pK_b$ of at least about 8.25, drug Y could be used to deprotonate drug X. Drug X would then have an enhanced rate of penetration into the skin. This can be particularly useful where drug Y is intended to act topically, is intended to be administered over a relatively longer period of time such that the salt form created is not a problem, or where the salt form of drug Y retains a relatively high rate of skin penetration. It may also be desirable to use two drugs with a $pK_b$ differential of less than about 0.75 so as to setup a competitive deprotonating reaction between them.

Again, the amount of biocompatible deprotonating agent in accordance with the present invention will vary with a number of factors. The amount will be very dependent upon the amount of pharmaceutically active agent utilized. Moreover, the strength or $pK_b$ differential between the deprotonating agent and the pharmaceutically active agent may also play a role in determining how much deprotonating agent is necessary. The range of deprotonating agent used will also vary with the stoichiometry of the deprotonation reaction. Generally, once the amount of protonated pharmaceutically active agents are selected, a stoichiometrically corresponding amount of deprotonating agent should be used. It may be desirable to add an excess of deprotonating agent relative to the amount of deprotonated pharmaceutically active agent so as to ensure a complete reaction.

Any of the formulations discussed herein may also include a viscosity modifier such as Fumed Silica such as Cabosil, adhesive compatible acrylic polymers such as Elvacite from DuPont, and vinyl polymers such as Polyvinyl Pyrrolidone (Plazdone C-30 from ISP), Ammonium Polyacrylates (such as Acrysol G-110 from Rohm and Haas), Hydroxy Propylcellulose (such as Klucel from Aqualon). The viscosity modifier may play a role in controlling release of the drug and/or the rate of the deprotonation reaction. Cross linkers such as: Metal Alkoxides (such as Isopropoxide), Melamine-based Polyols (such as Cylink HPC resins from Cytec Industries, Inc.), Organic Titanates (such as Tyzor from DuPont Chemicals) may also be used. The composition of the present invention may further include one or more Permeation Enhancers such as: Propylene Glycol, Polyethylene Glycol, unsaturated long-chain fatty acids (such as Oleic Acid), short-chain alcohols (such as Ethanol, Isopropanol, n-Butanol), Dimethylsulfoxide, Azone, N-Methyl-2-Pyrrolidone, Decylmethylsulfoxide, Anionic Surfactants (such as Sodium Lauryl Sulfate), Nonionic Surfactants (such as Polyoxyethylene (20) Sorbitan Monoleate), Cationic Surfactants (such as N,N-Bis(2-Hydroxyethyl)-Oleylamine), Zwitteronic Surfactants (such as Dodecyl-Dimethylammoniopropane Sulfate), Terpenes. These may be particularly useful when using a drug as a deprotonating agent as the delivery profile of the later protonated drug may be significantly enhanced. Anti-irritants such as Hydrocortisone, Flurbiprofen, and Indomethecin may also be useful.

The therapeutic formulation in accordance with the present invention can be made in a number of ways. A particularly preferred method, the deprotonating agent such as, for example, TEA or PEI, is mixed with a small amount of nonaqueous solvent such as, for example, 1,2 propanediol. This solution is then mixed into the acrylic adhesive base material. Thereafter, a pharmaceutically active agent in protonated form, such as, for example, selegiline-HCl, is dissolved in a nonaqueous solvent, and, preferably, the same nonaqueous solvent used to dissolve the deprotonating agent. Thereafter, the drug-containing solution is added to the mixture of the adhesive base and the dissolved deprotonating agent. While within the acrylic adhesive base, the selegiline-HCl and the deprotonating agent, i.e., TEA, react such that TEA-HCl and free selegiline are formed. The reaction kinetics of this reaction strongly favor these end products. Of course, the order of the addition of ingredients can vary. For example, the TEA solution can be added to the selegiline-HCl solution and then the resulting mix can be added to the adhesive.

Generally, all mixing is done at room temperature. However, the deprotonating reaction may be somewhat exothermic and, therefore, it may be advantageous to cool the mixture to prevent degradation of the drug. After the mixture in accordance with the present invention has been formed and while the deprotonating reaction is taking place, the material may be directly forwarded and introduced into a transdermal patch.

A typical patch is shown in FIG. 1. It includes a baking layer 1, a release layer 2 and a therapeutic adhesive formulation including both adhesive and drug in free form 3, disposed therebetween. In use, the release layer is peeled away exposing a surface of the adhesive which is then applied to the skin. The backing layer helps contain the material and prevent contamination. Any material useful in the production of transdermal patches can be used herein and almost any construction is appropriate In accordance with another aspect of the present invention, it is possible to deprotonate the protonated pharmaceutically active agent prior to its introduction into an admixture with the adhesive material. In this case, the pharmaceutically active agent and the deprotonating agent, as previously described herein, are mixed in a solvent until the reaction between the two components is complete. Generally, a stoichiometric or slightly greater amount of deprotonating agent is used relative to the amount of pharmaceutically active agent so as to insure that the equilibrium drives the deprotonating reaction to completion. Often, the consequence of this reaction will be the formation of crystals or a precipitate of the now protonated deprotonating agent. While there is generally no adverse consequence because of the inclusion of such crystals, it is preferred to minimize or entirely eliminate such crystals if possible. Accordingly, before the mixture is mixed into the adhesive material base, the mixture is centrifuged, filtered, or otherwise processed such that the solid crystals or precipitate are removed. The remaining solution comprising mainly solvent and deprotonated pharmaceutically active agent, along with some residual liquid deprotonating agent, is then mixed into the adhesive mixture and then used in the production of transdermal patches as previously described. It is also possible to remove any crystals or other solids from the adhesive before the adhesive is used to construct a transdermal patch. This is accomplished as previously discussed.

In accordance with another aspect of the present invention, it may also be desirable to control the rate of the deprotonating reaction and, therefore, the conversion of the protonated pharmaceutically active agent to the free form thereof. By this statement, it should be understood that the present invention is nonetheless different than the Heiber et al. patent previously discussed. In Heiber et al., a physical barrier is provided to stop substantially any reaction between the therapeutic agent and an activating agent therefor until just prior to use. The materials must be maintained completely separately starting from manufacture and continuing through storage up until the moment of use. In the present invention, even if steps are taken to control the rate of reaction, nonetheless, some reaction between the protonated form of the pharmaceutically active agent and the biocompatible deprotonating agent will take place during manufacture or not long thereafter. Additional conversion will take place during storage prior to use.

One method of controlling the rate of reaction was described previously and involves the use of PEI. Other cage-like deprotonating agents may also be used. Similarly, it may be possible to place either the pharmaceutically active agent or the biocompatible deprotonating agent inside of a microcapsule, microsphere, or matrix microparticle which somewhat restricts but does not completely eliminate the interaction of the two reactive species. The degree of permeability or the degree of dissolution of the microcapsule material will, at least in part, be rate controlling. Alternatively, the viscosity and/or degree of crosslinking of the adhesive material and/or the totality of the formulation can be increased or decreased. The greater the viscosity and/or molecular weight of the adhesive mixture, the greater the diffusion time for the various ingredients and the slower the time of reaction. Patches in accordance with the present invention can also be stored at generally lower temperatures which can also control the reaction of kinetics.

Another interesting method in accordance with the present invention involves separate formation of two or more layers of adhesive material in accordance with the present invention. One of the adhesive layers would include mixed therein the protonated form of the pharmaceutically active agent dissolved in a nonaqueous solvent. A second layer (adhesive or not) would include the biocompatible deprotonating agent dissolved in a nonaqueous solvent. These two layers could then be superimposed or placed in intimate contact with one another. Some reaction between the deprotonating agent in one layer and the pharmaceutically active agent in the adjacent layer will take place substantially immediately or shortly after contact. However, depending upon the design, the ratio of continued reaction may depend upon diffusion through the various layers. Eventually, the entirety of the pharmaceutically active agent will be deprotonated.

Figure 2:
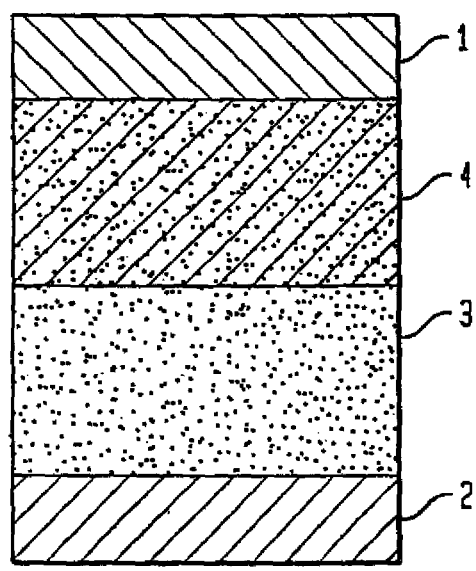
FIG. 2 is a side planar view of a drug delivery patch having plural layers in accordance with the present invention.

As shown in FIG. 2, a transdermal patch of this type includes a baking layer 1, a release layer 2 a first adhesive layer 3 adjacent the release layer and a second layer 4 disposed between the adhesive layer 3 and the backing layer 1. Second layer 4 may be an adhesive layer, but it need not be adhesive. The protonated drug is initially disposed in either layer 3 or layer 4 and the deprotonating agent is disposed in the other layer. Over time, as the drug is converted to free form, the distribution of the drug may vary within the layers. In use, the release layer 2 is peeled away exposing a surface of the first adhesive layer 3 which is then applied to the skin. The backing layer 1 helps contain the material and prevent contamination. Any material useful in the production of transdermal patches can be used herein and almost any construction is appropriate This later arrangement has additional benefits. Specifically, during the manufacture of an adhesive patch as described herein, after the adhesive mixture including the pharmaceutically active agent have been introduced into the patch or formed into a mold, the material is dried. During that drying, it is not uncommon for some of the pharmaceutically active agent to evaporate. This can cause the dosage form to be underweight in terms of the amount of therapeutic material delivered, or may force a manufacturer to incur additional costs by producing a wet mixture containing an excess of pharmaceutically active agent with the expectation that a percentage thereof will evaporate away. In accordance with one aspect of the present invention, however, the deprotonating agent and the pharmaceutically active agent are dissolved into two different layers, each of which is separately dried. Neither the deprotonating agent nor the protonated drug are as sensitive to the heat used in drying as the deprotonated pharmaceutically active agent. After drying, the individual layers can be brought into intimate contact with each other such that the deprotonating reaction can begin.

Finally, when the drug used is a highly plasticizing drug as defined herein, it may be added to the adhesive as either a free base form or as a protonated drug. In the case of the former, deprotonating agents, and possibly solvents, will not be necessary. In the case of the latter, as with any other protonated pharmaceutically active agent as defined herein, both solvent and deprotonating agent may be necessary.

Formulating patches including highly plasticizing drugs in free form tends to be a far simpler operation. The drug is merely mixed with an acrylic polymeric adhesive, as well as any other additional excipients, and then treated as any other material, using methods conventional in the manufacturing of transdermal patches. The material can be made into a film, dried into a block poured into a mold and the like.

EXAMPLES

Example 1

Three formulations were produced in accordance with the present invention. The formulations are shown in Table 4 below.

TABLE 4

| INGREDIENTS | WET BASIS | DRY BASIS* |
|---|---|---|
| Selegiline Base | 3.5 | 5 |
| GELVA 1753 | 119 | 85 |
| Selegiline Base | 6.74 | 10 |
| GELVA 1753 | 134.4 | 80 |
| Selegiline Base | 9.45 | 15 |
| GELVA 1753 | 105 | 15 |

*parts

Each formulation was prepared with the same protocol. An amount of liquid drug as indicated in Table 4 was weighed out. The indicated amount of dry adhesive was also weighed. The drug was slowly added to the adhesive while agitation continued moderately to create a homogenous blend. A thin film of the drug/adhesive blend was produced in a controlled thickness of between 70-95 mg/10 cm² to a thickness of onto a release-coated plastic/paper substrate using a knife-over-roll technique. The coating was then dried in an oven at between 110° and 140° F. to remove the solvents. The dry drug-polymer film was then laminated to a backing material made of PET/PE and die-cut into patches.

Example 2

Analytical Study of Conversion of Selegiline-HCl to Selegiline Free Base

Selegiline-HCl and one of the following deprotonating agents were added to water and analyzed for turbidity using standard protocols. The results are reported below in Table 5.

TABLE 5

| DEPROTONATING AGENT | $pK_b$ | TURBIDITY |
|---|---|---|
| Diethylamine | 3.07 | Yes |
| Triethylamine | 3.28 | Yes |
| Ethanolamine | 4.5 | Yes |
| Ammonia | 4.75 | Yes |
| Triethanolamine | 6.2 | Yes |
| Imidazole | 7.05 | Yes |
| Pyridine | 8.77 | Yes - Slight |
| Aniline | 9.34 | No |

Selegiline free base, i.e., in its deprotonated form is only sparingly soluble in water. For this reason it is important that the solvent used in accordance with the present invention be a nonaqueous solvent. Visual observations of the resulting mixtures indicated turbidity in most of the tested cases. Turbidity is attributable to the conversion of the selegiline-HCl which is readily soluble in water to the free base form which is not.

Selegiline free form or free base has a $pK_b$ value of approximately 9.0. As will be apparent from Table 5, pyridine having a $pK_b$ of 8.77 produced some slight turbidity indicating some level of conversion of the selegiline-HCl to selegiline free base. However, aniline having a $pK_b$ higher than selegiline, produced no turbidity indicating no conversion to the free base form. Imidazole having a $pK_b$ of 7.05 produced strong turbidity indicating significant conversion.

Diethylamine and triethylamine also produced significant turbidity indicating conversion of the selegiline-HCl to the free base form. However, because of their low $pK_b$, and their resulting high pH, these deprotonating agents would generally be inappropriate for use in accordance with the present invention. Of course, it is possible that certain patch formulations which will require only brief exposure to the skin or very low concentrations of active ingredient may allow for the use of such agents.

The test was repeated using propylene glycol as the test medium. Selegiline free base concentration was measured by UV absorbency of cyclohexane extract and compared with a stoichiometric value of selegiline free base. The results are illustrated in Table 6.

TABLE 6

| List | $pK_b$ | Selegiline Free Base Conversion |
|---|---|---|
| Imidazole | 7.05 | 100% |
| Pyridine | 8.77 | 15% |
| Aniline | 9.34 | 0% |

Imidazole having a $pK_b$ of 7.05 produced a selegiline conversion of approximately 100%. Pyridine having a $pK_b$ of 8.77 produced a selegiline free base conversion of 15%. Aniline having a $pK_b$ of 9.34 produced no conversion. This data strongly supports the visual observances of turbidity described above.

Example 3

Additional Analytical Testing

Additional testing was undertaken by dissolving various pharmaceutically active agents in a 25% solution of propylene glycol and analyzing them as described in Example 2. Triethylamine having a $pK_b$ of approximately 3.28 was capable of converting phenylpropranolol-HCl and propranolol-HCl (the free base forms having a $pK_b$ of 4 and 5 respectively). UV testing indicated that conversions were substantially complete. This shows that a $pK_b$ differential of about 0.75 (in the case of phenylpropranolol, a differential of 0.72) is necessary for complete conversion from the hydrochloride salt to the free base form.

Of course, triethylamine had a measured pH of approximately 11.7 and a calculated pH of approximately 13.7. Such material would generally be too caustic for use in accordance with the present invention, especially of the calculated pH value, except under specialized circumstances. An actual pH of 11.7 is acceptable, an actual pH of 13.7 is not. Similarly, phenylpropranolol-HCl generally requires the use of a deprotonating agent having a $pK_b$ which is so low that it may cause irritation. In addition, the free base form of this pharmaceutical itself has a pH of approximately 13 which is generally too caustic for use in accordance with the present invention.

Ammonia having a $pK_b$ of 4.75 was able to completely deprotonate verapamil-HCl (free base having a $pK_b$ of 6) and, partially deprotonate propanol (free base form having a $pK_b$ of 5). This also demonstrates that the $pK_b$ differential between the drug and the deprotonating agent needs to be approximately 0.75 or greater is useful to insure a complete reaction. Triethanolamine having a $pK_b$ of 6 was fully able to convert scopolamine-HCl and clonidine-HCl to their respective free base forms ($pK_b$ of 7-8 and 7 respectively).

Example 4

0.6 kg of selegiline HCl was dissolved in 1.17 kg of 1,2 Propanediol in a 2 gallon container, under mild agitation, using an air mixer. In a separate 2 liter container, 0.407 kg of TEA was mixed with 0.4 kg of Ethanol at ambient temperature using mild agitation from air mixer. In a separate 5 gallon container, 3.55 kg of liquid adhesive GELVA 1753 was placed and 0.5 kg of Ethanol was mixed in using a high shear mixer. After all the Ethanol was dissolved, the Ethanol solution of TEA from the 2 liter container was gradually mixed into the adhesive while continuously mixing using a high shear mixer (Sharr mixer). After complete addition of TEA solution, 1.2 Propanediol solution of selegiline HCl, from a 2 gallon container, was gradually added to the continuously mixed adhesive. The mixing continued until a homogenous mixture was realized (about 30 minutes). Final adhesive mixture was coated (using knife-over-roll coating method) on a siliconized release liner and dried continuously in the 3 zone oven and "in line" laminated to a backing layer such as 1 mil Polyester. This laminate was subsequently die cut into round 10 cm² patches and packaged in heatsealable pouches.

Example 5

The procedure used in example 4 was repeated. However, 3.6 kg of selegiline HCl was dissolved in 6.3 kg of 1,2 Propanediol. Accordingly, the amount of TEA was increased from 0.407 kg to 2.44 kg and mixed with 2.4 kg of Ethanol. The amount of GELVA 1753 adhesive was increased to 21.0 kg and diluted with 3.0 kg of Ethanol. The adhesive mixture was agitated using Sharr Mixer while both solutions of selegiline HCl and TEA were subsequently added into mix as described in Example 4. The coating, drying, laminating was done as described in Example 4. Die cutting of the laminate and pouching of the patches were done as described in Example 4.

Example 6

17.773 kg of selegiline HCl was dissolved in 34.55 kg 1,2 Propanediol under mild agitation using an air mixer. In a separate container, 12.046 kg of TEA was mixed with 12.046 kg of Ethyl Alcohol and mixed using an air mixer. In a separate 10 gallon mixer, 16.05 kg of GELVA 1753 was placed and 5.7 kg of Ethanol was mixed in. While mixing 3.65 kg of the TEA solution was added to the adhesive mix and mixed very well using Sharr mixer. 7.926 kg of selegiline HCl solution was added. The mixing was continued until an homogenous mixture was obtained. The final mixture was pumped into the centrifuge and crystals of TEA HCl were separated from the clear adhesive mix at 17,000 rpm. The clear adhesive mix containing Selegiline Free Base was collected in a separate container. The clear adhesive mixture was coated, dried and laminated as described in Example 4. Die cutting of the laminate and pouching of the patches were done as described in Example 4.

Example 7

8.82 kg of selegiline HCl was dissolved in 16.92 kg of Propanediol in a stainless steel container under mild agitation using air mixer. 5.98 kg of TEA was mixed with 5.98 kg of Ethyl Alcohol in a stainless steel container under mild agitation using air mixer at 600 rpm. The contents of the two containers were then mixed together while mixing the selegiline HCl solution, the TEA solution was added gradually for about 10 minutes and then allowed to stand for a minimum of 8 hours. The above solution containing slurries of TEA HCl crystals were pumped to a centrifuge at a low rate. The centrate was separated and collected in a 10 gallon stainless steel container. The 10.91 kg of the centrate was dispersed in 59.3 kg of GELVA 1753 in a separate container using Sharr mixer. The mixing was continued until a homogenous adhesive mixture was realized. The adhesive mixture was coated, dried and laminated as described in Example 4. Die cutting of the laminate and pouching of the patches were done as described in Example 4.

Example 8

18 grams of selegiline HCl was dissolved in 35 grams of 1.2 Propanediol at about 40° C. in a 100 ml beaker under mild agitation using a magnetic stirrer. In a separate 150 ml beaker, 48.35 grams of GELVA 1753 adhesive was mixed with 17.33 grams of 1,2 Propanediol solution of selegiline HCl. After completion of mixing the adhesive mixture containing selegiline HCl was coated on a siliconized release liner using a laboratory knife-over-roll coater, dried in the oven and laminated to 1 mil polyester film. The coat weight of adhesive was about 100 mg per 10 cm². This was "Part A" of the final patch. 24.4 grams of TEA were mixed with 20 ml of 1.2 Propanediol in a 100 ml beaker. In a separate 150 ml beaker 42.9 g of GELVA 1753 adhesive was mixed with 11.1 g of 1,2 Propanediol solution of TEA. After completion of mixing, the adhesive mixture containing TEA was coated on a siliconized release linear using a laboratory knife-over-roll coater, and dried in the oven. The coat weight of adhesive was 50 mg per 10 cm². This was "Part B" of the final patch. After removing the release liner, the adhesive layer of "Part A" was laminated to adhesive layer "Part B". This laminate was allowed to age at room temperature for 3 days. After that, 10 cm² round patches were die cut and extracted in cyclohexane. The resulting free base of selegiline was analyzed. The conversion rate of selegiline HCl into selegiline free base was found to be 83%.

(Examples 9 through 18 relate to the formulations described in Table 3.)

Example 9

1.07 kg of selegiline free base was added to 10.9 kg of GELVA 1753 acrylic polymeric adhesive; both were in liquid form. The resulting therapeutic adhesive formulation was coated onto a polyester release liner using a knife-over-roll technique at 93 mg/10 cm² target coat weight and the result was dried. The resulting therapeutic adhesive formulation included 18 mg/10 cm² (dry) of selegiline and 72 mg/cm² (dry) of adhesive. The dried film was then laminated onto a clear PET/EVA backing material. The resulting patches exhibited acceptable drug storage stability as defined by the U.S. Food and Drug Administration for this class of transdermal patches and drug delivery profile. The resulting patches were able to remain on skin for at least 24 hours, exhibited no peeling or oozing, left no adhesive residue on the skin when removed and were removable without injury to the skin. Note that this therapeutic adhesive formulation does not include solvents other than those which are part of the commercially available adhesive and that the system is anhydrous. Substantially, all liquids in the system are removed by drying. However, some trace amounts of either liquid or solvent may still be present.

Example 10

130.5 parts of GELVA 1753 were mixed with 7.41 parts of selegiline free base and 20 parts of ethanol. The resulting therapeutic adhesive formulation was coated onto a polyester release liner and dried at 130° F. for 4 minutes. The dried film was then laminated on a PET backing. The resulting patches included approximately 15 mg/10 cm² (dry). The resulting patches were able to remain on skin for at least 24 hours, exhibited no peeling or oozing, left no adhesive residue on the skin when removed and were removable without injury to the skin. This therapeutic adhesive formulation was produced with ethanol as an added solvent. That solvent, as well as the solvents found in the commercial adhesive were evaporated during drying. The resulting formulation contains substantially no water or non-volatile liquids after drying. However, some trace amounts of either liquid or solvent may still be present.

Example 11

4.91 parts of selegiline free base and 20 parts by weight of ethanol were mixed with 136.75 parts of GELVA 1753 using the process described immediately in Example 10. The resulting patches contained a therapeutic formulation including approximately 10 mg/10 cm$^2$ (dry) of selegiline. The resulting patches were able to remain on skin for at least 24 hours, exhibited no peeling or oozing, left no adhesive residue on the skin when removed and were removable without injury to the skin.

Example 12

109 parts of GELVA 1753 were mixed for one hour with 10 parts of propylene glycol, 5 parts of selegiline base and parts of ethanol. The resulting therapeutic adhesive formulation was then coated onto a polyester release liner using a bench-top knife-over-roll coater and dried in an oven at 130° F. for four minutes. The dried film was laminated onto a PET backing. The dried film had a composition of approximately 8% selegiline and 10% PG, i.e., approximately 8 mg/10 cm$^2$ (dry). Like all of the other formulations including GELVA 1753, this formulation was acceptable in terms of adhesive transfer and oozing. However, unlike the 10% and 15% formulations (each of which were formulated with a volatile solvent), the adhesive properties of the patches resulting from this batch were found to be unacceptable. The PG remained as part of the formulation after drying and acted with the selegiline in such a way that it retarded adhesion.

Example 13

10 parts of PG, 5 parts of selegiline free base, 20 parts of ethanol, and 77.8 parts of DUROTAK 87-2194 were mixed and processed as described above in Example 10. As shown in Table 3, the formulation exhibited cohesive failure and adhesive transfer.

Example 14

83.33 parts of DUROTAK 87-2516 adhesive, 10 parts of PG and 5 parts of selegiline base, as well as 20 parts of ethanol were mixed as previously discussed and coated, using a bench-top knife-over-roll device, on a polyester release liner and dried in an over at 130° F. for four minutes. The dried film was then laminated to make PET backing. The resulting formulation contained approximately 8 mg/10 cm$^2$ (dry) of selegiline. As demonstrated in Table 3, patches made from this formulation exhibited adhesive transfer when applied to the skin.

Example 15

85.37 parts of GELVA 788 adhesive, 10 parts of PG, 5 parts of selegiline base and 20 parts of ethanol were mixed an processed as described in Example 14. Again, the therapeutic adhesive formulation included approximately 8 mg/10 cm$^2$ (dry) of selegiline and again adhesive transfer was found to result when these patches were applied to skin.

Example 16

1.07 kg of selegiline was added to 8.78 kg of GELVA 655 liquid adhesive with constant mixing. The resulting therapeutic adhesive formulation was then coated onto a silicone coated polyester release liner using a knife-over-roll technique at 93 mg$^{+4}$/10 cm$^2$ target coat weight and dried. The dried film was laminated to a PET/EVA backing. The resulting patches included 18 mg/10 cm$^2$ (dry) of selegiline. As demonstrated in Table 3, this formulation exhibited total adhesive failure.

Example 17

0.7 kg of selegiline was mixed with 11.1 kg of DUROTAK 87-2852 liquid adhesive and processed as above in Example 16. A polyester release liner was used. The resulting therapeutic adhesive formulation included 12 mg/10 cm$^2$ (dry) of selegiline. As shown in Table 3, no adhesive transfer or oozing was realized. This material was made without any solvent other than that provided as part of the adhesive and it exhibited acceptable adhesion results as described in Example 9

Example 18

1.07 kg of selegiline was added to 10.29 kg of adhesive and processed as above in Example 16. The resulting therapeutic adhesive formulation included 18 mg/10 cm$^2$ (dry) of selegiline. The release liner used was a silicone coated release liner. As shown in Table 3, this formulation, by virtue of the higher concentration of highly plasticizing drug, showed some softness.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A transdermal delivery system comprising a blend of
(a) one or more hydrophobic adhesive polymers; and
(b) a therapeutically effective amount of one or more drugs, at least one of which is of low molecular weight and liquid at or about room temperatures,
said system comprising solvents consisting essentially of at least one solvent which volatilizes during drying at a temperature of between about 100° F. and 200° F.
2. The transdermal delivery system of claim 1 wherein said solvents volatilize during drying at a temperature of between about 100° F. and 140° F.
3. The transdermal delivery system of claim 1 wherein said one or more drugs comprises one or more highly plasticizing drugs.
4. The transdermal delivery system of claim 3 wherein said highly plasticizing drugs are selected from the group consisting of selegiline, fluoxetine, des-methyl selegiline, tetracaine and chlorpheniramine.
5. The transdermal delivery system of claim 1 wherein said one or more hydrophobic adhesive polymers comprises acrylic polymers.
6. The transdermal delivery system of claim 1 comprising from about 3% to 35% by weight of said therapeutically effective amount of one or more drugs.
7. The transdermal delivery system of claim 4 wherein said drug comprises selegiline.
8. The transdermal delivery system of claim 7 including from about 3% to 18% by weight of said selegiline.

9. A transdermal delivery system comprising a blend of
(a) one or more hydrophobic acrylic adhesive polymers and one or more secondary adhesive polymers; and
(b) a therapeutically effective amount of one or more drugs, at least one of which is of low molecular weight and liquid at or about room temperature,
said system comprising a solvent system consisting essentially of at least one solvent which volatilizes during drying of said transdermal delivery system at temperatures of from about 100° F. to 200° F.

10. The transdermal delivery system of claim 9 wherein said one or more secondary adhesive polymers is selected from the group consisting of silicones, polyisoalkylenes, rubbers, vinyl acetates, polyisobutylenes, polybutadiene, styrene-butadiene (or isoprene)-styrene block copolymer rubber, acrylic rubber, natural rubber, vinyl-based high molecular weight materials, polyvinyl acetate, polyvinyl alcohol, polyvinyl pyrrolidone; cellulose derivatives, polysaccharides, polyurethane elastomers and polyester elastomers.

11. The transdermal delivery system of claim 10 wherein said one or more secondary adhesive polymers is selected from the group consisting of polyisobutylenes and silicones.

\* \* \* \* \*